(12) United States Patent
Fischer et al.

(10) Patent No.: US 9,037,237 B2
(45) Date of Patent: May 19, 2015

(54) ALGORITHM TO MODULATE ATRIAL-VENTRICULAR DELAY AND RATE RESPONSE BASED ON AUTONOMIC FUNCTION

(75) Inventors: Trent M. Fischer, St. Paul, MN (US); Douglas A. Hettrick, Andover, MN (US); Todd J. Sheldon, North Oaks, MN (US); Paul A. Belk, Maple Grove, MN (US); Thomas J. Mullen, Andover, MN (US); John C. Rueter, Woodbury, MN (US); Daniel R. Kaiser, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1057 days.

(21) Appl. No.: 12/787,058

(22) Filed: May 25, 2010

(65) Prior Publication Data

US 2011/0029034 A1 Feb. 3, 2011

Related U.S. Application Data

(60) Provisional application No. 61/229,409, filed on Jul. 29, 2009.

(51) Int. Cl.
*A61N 1/368* (2006.01)
*A61N 1/362* (2006.01)
*A61N 1/365* (2006.01)
*A61B 5/0456* (2006.01)

(52) U.S. Cl.
CPC ............ *A61N 1/3627* (2013.01); *A61B 5/0456* (2013.01); *A61N 1/36514* (2013.01); *A61N 1/36542* (2013.01); *A61N 1/36557* (2013.01); *A61N 1/36564* (2013.01); *A61N 1/36571* (2013.01); *A61N 1/36578* (2013.01); *A61N 1/36585* (2013.01); *A61N 1/368* (2013.01); *A61N 1/3682* (2013.01); *A61N 1/3688* (2013.01)

(58) Field of Classification Search
USPC ............................................. 607/9, 17, 23, 27
See application file for complete search history.

(56) References Cited

U.S. PATENT DOCUMENTS

| | | | |
|---|---|---|---|
| 5,179,949 A | 1/1993 | Chirife | |
| 5,247,930 A | 9/1993 | Begemann et al. | |
| 5,454,838 A | 10/1995 | Vallana et al. | |
| 5,534,017 A | 7/1996 | van Krieken et al. | |
| 5,562,711 A | 10/1996 | Yerich et al. | |
| 5,626,623 A | 5/1997 | Kieval | |
| 5,861,007 A | 1/1999 | Hess et al. | |

(Continued)

FOREIGN PATENT DOCUMENTS

EP 0970721 A2 1/2000

OTHER PUBLICATIONS (PCT/US2010/039202) PCT Notification of Transmittal of the International Search Report and the Written Opinion of the International Searching Authority, Mailed Sep. 10, 2010, 8 pages.

*Primary Examiner* — Christopher D Koharski
*Assistant Examiner* — Michael D Abreu
(74) *Attorney, Agent, or Firm* — Michael C. Soldner

(57) ABSTRACT

An implantable medical device and associated method provide atrial pacing and measure an atrial ventricular (AV) delay. An autonomic function index is computed using the AV delay. The autonomic function index may be compiled in a medical report. In some embodiments, the autonomic function index is used to adjust atrial pacing control parameters.

22 Claims, 10 Drawing Sheets

(56) References Cited

U.S. PATENT DOCUMENTS

| | | |
|---|---|---|
| 6,669,645 B2 | 12/2003 | Narimatsu |
| 6,772,005 B2 | 8/2004 | Casavant et al. |
| 7,130,683 B2 | 10/2006 | Casavant |
| 7,218,965 B2 | 5/2007 | Casavant et al. |
| 7,218,968 B2 | 5/2007 | Condie et al. |
| 7,248,924 B2 | 7/2007 | Casavant et al. |
| 7,480,528 B2 | 1/2009 | Brockway et al. |
| 7,483,743 B2 | 1/2009 | Mann et al. |
| 7,505,813 B1 | 3/2009 | Gill et al. |
| 7,509,170 B2 | 3/2009 | Zhang et al. |
| 2002/0151938 A1 | 10/2002 | Corbucci |
| 2003/0088288 A1 | 5/2003 | Armstrong et al. |
| 2005/0055060 A1* | 3/2005 | Koh et al. .......... 607/17 |
| 2007/0093874 A1 | 4/2007 | Lundstrom |

* cited by examiner

US 9,037,237 B2

ALGORITHM TO MODULATE ATRIAL-VENTRICULAR DELAY AND RATE RESPONSE BASED ON AUTONOMIC FUNCTION

CROSS REFERENCE TO RELATED APPLICATION

This application claims the benefit of U.S. Provisional Patent Application No. 61/229,409, filed Jul. 29, 2009, the disclosure of which is incorporated by reference herein in its entirety.

TECHNICAL FIELD

The disclosure relates generally to implantable medical devices and, in particular, to implantable medical devices having rate response capabilities.

BACKGROUND

Naturally conducted or intrinsic ventricular depolarizations have been recognized as being preferable over ventricular pacing in general and pacing in the right ventricular apex in particular. In order to minimize or greatly reduce ventricular pacing, protocols have been developed that, in general, utilize an atrial based timing mode that promotes intrinsic conduction whenever possible. Illustrative protocols are described in U.S. Pat. No. 7,218,965 (Casavant), U.S. Pat. No. 6,772,005 (Casavant), and U.S. Pat. No. 7,248,924 (Casavant), all of which are incorporated herein by reference in their entireties.

Atrial based pacing in general, as well as in the context of minimizing ventricular pacing as discussed above, may also include a rate response function. As a metabolic demand sensor indicates a need for increased cardiac output, the heart rate is elevated by increasing the atrial pacing rate. However, without ventricular pacing, there is no control over the ventricular timing. As such, if the intrinsically conducted ventricular event results in an atrial to ventricular delay (AV delay) that is not shortened, or is actually elongated by the AV node in response to the elevated pacing rate, overall timing of the cardiac chamber contractions may become skewed. That is, the A-A interval is decreasing but the AV delay is not correspondingly and correctly modified. As a consequence, VA delay (ventricular to atrial interval) may be shortened. Another consequence may be Wenckebach block in which given ratios of ventricular beats are not conducted with respect to the atrial rate. As such, even though the atrial rate may rise, the effective ventricular rate could actually decrease.

If the VA delay becomes too short over a prolonged period of time, negative consequences may result. The contraction of the ventricles takes a finite amount of time from initiation of a depolarization. If the contraction is not completed, a subsequent atrial contraction will attempt to force blood into a contracted ventricle, against a closed valve. Often, this results in retrograde blood flow out of the atria and back toward the lungs and venous system, which can become symptomatic. Similarly, the ventricles even if not fully contracted may not be fully relaxed during the atrial contraction, resulting in diminished filling. The net effect of having inadequate VA delay is that the elevation in heart rate fails to increase cardiac output, may actually reduce cardiac output, may result in hemodynamic compromise, and/or cause adverse patient symptoms.

DETAILED DESCRIPTION

Figure 1:
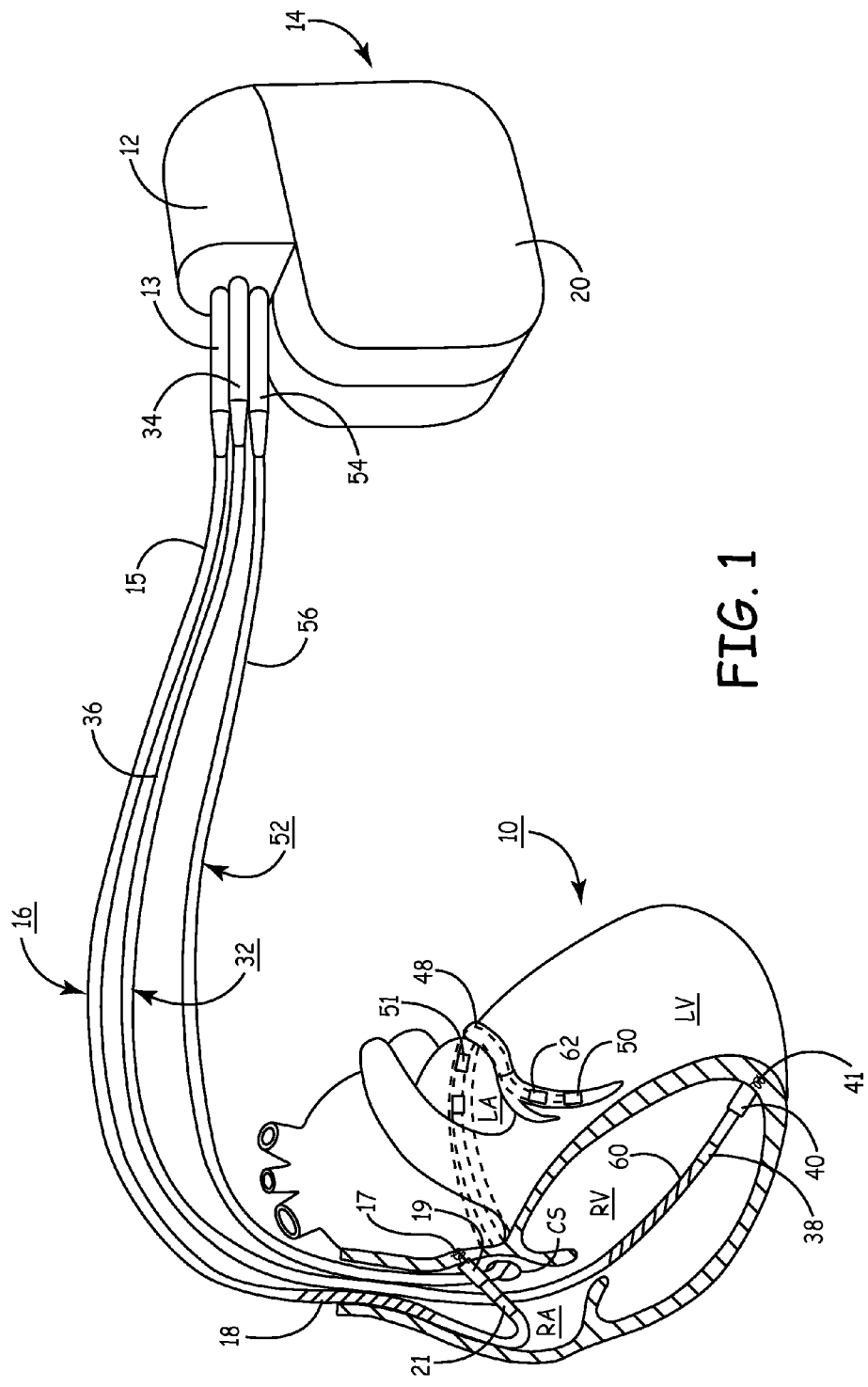
FIG. 1 depicts an implantable, cardiac stimulation device embodied in which monitoring and pacing methods described herein may be implemented.

In the following description, references are made to illustrative embodiments. It is understood that other embodiments may be utilized without departing from the scope of the disclosure. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

As used herein, an atrial based pacing mode is a mode that is programmed to pace in the atria, but only to sense in the ventricles. True single chamber atrial pacing would imply that only a single lead is present and ventricular activity may not be sensed in the ventricle nor would ventricular pacing be deliverable. In the present context an IMD operating in an atrial based mode includes at least ventricular sensing capabilities. Though not required, such a device would generally include ventricular pacing as well. However, in order to deliver ventricular pacing the device would switch pacing modes from the atrial only pacing mode to a dual chamber pacing mode, such as DDD.

As used herein, "atrial-ventricular delay" (AV delay) refers to the time between an atrial event and a subsequent ventricular sensed event (R-wave) conducted intrinsically from the atria to the ventricles. Thus an AV delay refers to a measured time interval between the atrial event and intrinsic ventricular depolarization in the absence of ventricular pacing. The atrial event may be a paced event or a sensed event, though in most applications discussed herein the atrial event will be a paced event during atrial rate responsive pacing. To differentiate between a "delay", which is measured between an atrial event and a ventricular sensed event, the term "interval" is used to refer to an interval that is timed out by the pacing device using escape interval timers for the purposes of delivering a pacing pulse. As such, an AA interval, an AV interval or a VA interval refers to intervals which upon expiration results in delivery of a pacing pulse. At the end of an AV interval, a ventricular pacing pulse is delivered. At the end of an AA interval, an atrial pacing pulse is delivered.

FIG. 1 depicts an implantable medical device (IMD) 14 in which monitoring and pacing methods described herein may be implemented. Various embodiments of the disclosure may be implemented in numerous types of implantable medical devices capable of sensing cardiac signals, such as pacemakers, ECG monitors, and hemodynamic monitors. IMD 14 is provided for sensing intrinsic heart activity and delivering cardiac stimulation pulses in the form of pacing, cardioversion or defibrillation therapy, as appropriate, to one or more heart chambers.

IMD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect IMD 14 with the RA, the RV and the LV, respectively. Each lead has at least one electrical conductor and pace/sense electrode. A remote indifferent can electrode is formed as part of the outer surface of the IMD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber and may be attached at its distal end to the RA wall using a fixation member 17. RA lead 16 is formed with a connector 13 fitting into a connector bore of IMD connector block 12 for electrically coupling RA tip electrode 19 and RA ring electrode 21 to IMD circuitry housed within housing 20 via insulated conductors extending within lead body 15. RA tip electrode 19 and RA ring electrode 21 may be used in a bipolar fashion, or in a unipolar fashion with IMD housing 20, for achieving RA stimulation and sensing of RA EGM signals. RA lead 16 is optionally provided with a coil electrode 18 that may be used for delivering high voltage cardioversion/defibrillation pulses to heart 10 in response to the detection of tachycardia or fibrillation.

RV lead 32 is passed through the RA into the RV where its distal end, carrying RV tip electrode 40 and RV ring electrode 38 provided for stimulation in the RV and sensing of RV EGM signals, is fixed in place in the RV apex by a distal fixation member 41. RV lead 32 optionally carries a high-voltage coil electrode 60 for use in cardioverting and defibrillating heart 10. RV lead 32 is formed with a connector 34 fitting into a corresponding connector bore of IMD connector block 12. Connector 34 is coupled to electrically insulated conductors within lead body 36 and connected with distal tip electrode 40, ring electrode 38 and coil electrode 60.

RV lead 32 additionally carries a physiological sensor 70 for sensing signals relating to the contraction of the ventricles. Sensor 70 may be a pressure sensor for measuring intra-cardiac ventricular pressures. Sensor 70 is coupled to IMD 14 via a conductor extending through lead body 36. In alternative embodiments, any of leads 16, 32 and 52 may carry a physiological sensor producing a signal responsive to the hemodynamic function of the heart 10. As will be described in detail herein, a hemodynamic signal may be used in conjunction with a sensed EGM signal for determining AV delay limits defined for intrinsically conducted ventricular depolarizations. Physiological sensor signals that may be used in measuring time intervals in conjunction with EGM signals include pressure signals for detecting the onset of pressure development associated with mechanical heart contraction, heart wall motion signals, flow signals associated with filling and ejection of blood from the heart, impedance signals for determining heart chamber volume, and acoustical signals for detecting heart sounds. Such signals can generally be used in identifying the timing of the mitral valve and/or tricuspid valve opening and closure.

Methods described herein are aimed at preventing atrial contraction against a closed atrioventricular valve, namely the mitral valve, located between the left atrium and left ventricle, or tricuspid valve, located between the right atrium the right ventricle. Such methods can be implemented to modulate the AV delay during atrial pacing modes, particularly in patients experiencing worsening autonomic function. While only one physiological sensor 70 is shown in FIG. 1, it is recognized that various embodiments may utilize one or more physiological sensors for detecting atrioventricular valve opening and closure. Physiological sensors may be located on a transvenous lead, an epicardial lead, a subcutaneous lead, in or on the housing of the IMD 14, or leadless sensors bodies communicating with IMD 14 via telemetry.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of IMD connector block 12 to provide electrical coupling of conductors extending from electrodes 50 and 62 within lead body 56 to IMD internal circuitry. In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the lead-mounted electrodes, IMD 14 may include one or more subcutaneous cardiac sensing electrodes (not shown) formed as uninsulated portions of the IMD housing 20 or included in the connector block 12. While a particular IMD system with associated leads and electrodes is illustrated in FIG. 1, numerous implantable cardiac monitoring, pacemaker and IMD system configurations are possible, which may include one or more leads deployed in transvenous, subcutaneous, or epicardial locations. The lead and electrode arrangements will depend on the particular application. Methods described herein may also be implemented in a subcutaneous cardiac monitor, pacemaker or IMD system in which electrodes are formed as a part of the device housing and/or carried by subcutaneous leads.

IMD 14 is shown as a multi-chamber device capable of sensing and stimulation in three or all four heart chambers. It is understood that IMD 14 may be modified to operate as a dual chamber device or a single chamber device having dual chamber sensing capabilities. In the illustrative embodiments, described herein, methods for monitoring autonomic function and modulating the AV delay generally relate to a pacemaker or IMD having at least dual chamber sensing and pacing. It is contemplated that the methods described, however, may be adapted for use in a single chamber device by using far-field sensing of ventricular events or using a hemodynamic signal for identifying the timing of ventricular mechanical events.

Figure 2:
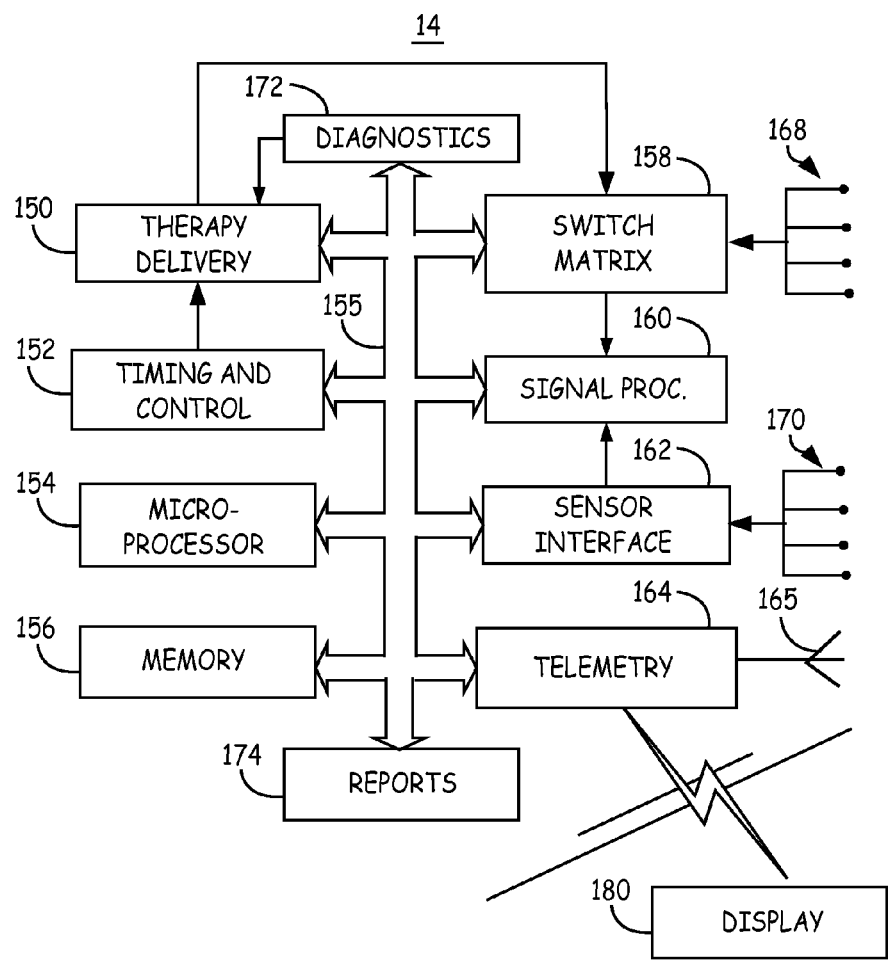
FIG. 2 is a functional block diagram of the IMD shown in FIG. 1 according to one embodiment.

FIG. 2 is a functional block diagram of the IMD 14 shown in FIG. 1 according to one embodiment. IMD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 14 via a data/address bus 155. IMD 14 includes therapy delivery module 150 for delivering electrical stimulation therapies, such as cardiac pacing therapies and arrhythmia therapies including cardioversion/defibrillation shocks and anti-tachycardia pacing (ATP), under the control of timing and control 152. Therapy delivery module 150 is typically coupled to two or more electrodes 168 via an optional switch matrix 158. Electrodes 168 may correspond to any of the electrodes shown in FIG. 1. Switch matrix 158 may be used for selecting which electrodes and corresponding polarities are used for delivering electrical stimulation pulses.

Cardiac electrical signals are sensed for use in determining when an electrical stimulation therapy is needed and in controlling a stimulation mode and the timing of stimulation pulses. Electrodes 168 used for sensing are coupled to signal processing circuitry 160. Signal processor 160 includes sense amplifiers and may include other signal conditioning circuitry and an analog-to-digital converter. Electrical signals may then be used by microprocessor 154 or other control circuitry for detecting physiological events, such as detecting and discriminating cardiac arrhythmias or detecting the need for pacing. Signal processing circuitry 160 may include event detection circuitry generally corresponding to R-wave detection circuitry as disclosed in U.S. Pat. No. 5,117,824 (Keimel, et al.), hereby incorporated herein by reference in its entirety.

IMD 14 is additionally coupled to one or more physiological sensors 170. Physiological sensors 170 may include at least one sensor responsive to cardiac hemodynamic function. In one embodiment, sensors 170 include a pressure sensor adapted for placement within a ventricle of the heart as shown in FIG. 1 for providing an intraventricular pressure signal. In other embodiments, sensors 170 may include a motion sensor such as an accelerometer, a flow sensor, blood chemistry sensors such as an oxygen saturation sensor, activity sensors, an acoustical sensor, or other physiological sensors. Physiological sensors may be carried by any lead extending from IMD 14, incorporated in or on the IMD housing or may be embodied as leadless sensors implanted in the body and in telemetric communication with the IMD or another device.

As will be described in detail herein, a hemodynamic signal acquired from physiological sensors 170 may be used in determining AV delay limits used in controlling rate responsive pacing. As used herein, the term "hemodynamic signal" refers generally to a signal measuring effects of the mechanical pumping function of the heart. A hemodynamic signal may be, but not necessarily limited to, a motion signal, a pressure signal, a flow signal, or an acoustical signal. Accordingly, hemodynamic sensors include sensors generating a signal corresponding to heart or vessel wall motion, arterial or intracardiac blood pressure, blood flow, or heart sounds. The hemodynamic signal may be used in particular to identify the onset of ventricular systole, e.g. as associated with mitral valve closure. As will be described herein, AV delay limits are defined to avoid atrial contraction against a closed valve or contracted ventricle, which may lead to retrograde flow and poor ventricular filling.

Signals from sensors 170 are received by a sensor interface 162 which provides sensor signals to signal processing circuitry 160. Sensor signals are used by microprocessor 154 for detecting physiological events or conditions. For example, IMD 14 may monitor heart wall motion, blood pressure, blood chemistry, respiration, or patient activity. Monitored signals may be used for sensing the need for delivering or adjusting a therapy under control of microprocessor 154. Monitored sensor signals may be analyzed to obtain diagnostic or prognostic data stored by IMD and made available to a clinician.

In various embodiments, IMD 14 includes rate responsive pacing in which an activity sensor, oxygen sensor, respiration sensor, or other sensor generating a signal correlated to changes in metabolic demand, referred to herein generally as "demand sensor", or any combination of demand sensors, is used to compute a sensor-indicated rate (SIR). Timing and control module 152 responds to the SIR by adjusting an atrial pacing rate up or down between a programmed lower rate and a maximum upper rate.

Diagnostic module 172 receives sensor signals for monitoring physiological variables. For example, variables relating to the patient's heart rhythm, hemodynamic performance, respiration or the like may be monitored to provide diagnostic and/or prognostic information for a clinician. Autonomic function can reflect the patient's over all disease state. As autonomic function worsens, the patient's cardiac disease state worsens. Autonomic function is reflected in the AV delay response to changing heart rate. In a normal patient, the AV delay shortens with increasing heart rate. An AV delay that does not shorten as expected, or even lengthens, in response to an increase in heart rate, could be evidence of worsening of autonomic function. Diagnostics module 172 monitors the patient's disease state by measuring an index of autonomic function. In one embodiment, this index is determined by measuring the AV delay at different AA intervals (i.e. at different heart rates) to determine the AV delay response to changes in heart rate. A worsening of "autonomic function" as used herein may include a worsening of the AV nodal function without a worsening of systemic autonomic function since the AV node could be diseased and thus less responsive to autonomic control.

Diagnostics module 172 may store an autonomic function index and determine a trend in the index over time. Reporting module 174 may compile patient and device-related data, including autonomic function index data, for reporting to a clinician. Changes in the autonomic function index may also be used by microprocessor 154 to alter control parameters stored in memory 156 or used by timing and control module 152 for controlling therapy delivery parameters. For example, a worsening in autonomic function may warrant changes in the timing and/or aggressiveness of rate response pacing therapy delivered to the patient's heart. Rate responsive therapy control parameters may be adjusted to provide less aggressive rate responsive pacing.

As will be described in detail below, less aggressive rate responsive pacing can be achieved, for example, by lowering an upper rate limit, lowering an activities of daily living setting, and/or adjusting the slope of a transfer function applied to a demand sensor signal for setting the pacing rate. Less aggressive rate responsive pacing may alternatively or additionally be achieved by altering the demand sensor(s) used for computing a sensor indicated rate or by altering the computations applied to the demand sensor signal(s) for computing the sensor indicated rate.

The IMD operating system includes associated memory 156 for storing a variety of programmed-in operating mode and parameter values that are used by microprocessor 154. Algorithms and control parameters used for determining a SIR and delivering rate responsive pacing, detecting arrhythmias, delivering arrhythmia therapy, monitoring AV delay, and monitoring autonomic function may be stored in memory 156. The memory 156 may also be used for storing data compiled from sensed EGM and physiological signals and/or relating to device operating history for telemetry out on receipt of a retrieval or interrogation instruction.

IMD 14 further includes telemetry circuitry 164 and antenna 165. Programming commands or data are transmitted during uplink or downlink telemetry between IMD telemetry circuitry 164 and external telemetry circuitry included in a programmer or monitoring unit. Report module 174 may compile data acquired by the IMD 14 for transmitting via telemetry circuitry 164 to an external display 180, which may be implemented in a programmer, personal computer, web-based or local network, or other communication device in communication with IMD 14. In one embodiment, data relating to an autonomic function index or trend in autonomic function index is compiled in a medical report that is transmitted to display 180 to be presented in a text or graphical display to a clinician.

Figure 3:
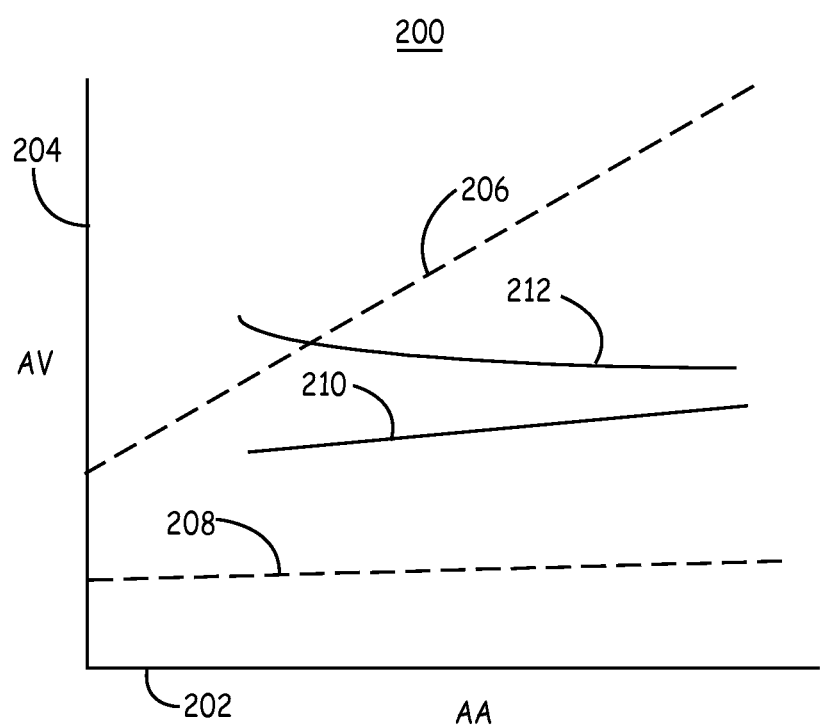
FIG. 3 is a graph of the AV response to changing AA intervals.

FIG. 3 is an illustrative graph 200 of the AV response to changing AA intervals in one subject. AV delay is plotted on the y-axis 204 and the corresponding AA interval is plotted on the x-axis 202. In the example shown, the AA intervals may be paced AA intervals and the AV delay is the time between the atrial pacing pulse and the subsequent, intrinsically-conducted, ventricular R-wave.

A normal physiological shortening of the AV delay with increasing heart rate, i.e. shorter AA intervals, is represented by the normal response 210, which has a generally positive, upward slope. In contrast, an abnormal response 212 is shown in which AV delay does not shorten with shorter paced AA intervals and may actually increase with faster pacing rates. While it is recognized that if the pacing rate is increased too quickly, even a healthy heart may not be able to quickly adjust with an appropriate AV delay, however, in patient's having poor autonomic function, the AV delay may not shorten even with more gradual increases in pacing rate as illustrated by FIG. 3.

The lengthening of the AV delay with shorter AA intervals can result in retrograde atrial flow and poor ventricular filling when the ventricle is still contracting upon the onset of the next atrial contraction. In some patients, pacing of the atrium at increasing rates based on a SIR computed from a demand sensor output can result in an abnormal AV delay response 212 as generally illustrated in FIG. 3. This abnormal response is a manifestation of worsening autonomic function. Accordingly, changes in the AV delay with changing AA intervals can be used to monitor the patient's autonomic function as indication of the patient's overall disease state. Monitoring the AV delay may also be used to adjust atrial rate response pacing to modulate the AV delay within a normal range, without necessarily converting to ventricular pacing to control AV intervals.

One approach to avoiding undesirably long AV delays is to initiate dual chamber pacing in which the AV interval is controlled by delivering a ventricular pacing pulse at an appropriate interval following the atrial pacing pulse. However, intrinsic conduction to the ventricles is generally preferred over ventricular pacing in patient's having intact AV conduction. Accordingly, alternative approaches for modulating the AV interval within a desired range will be described herein. As will be described in greater detail, an upper limit bound 206 and a lower limit bound 208 of acceptable AV delays may be defined. When the AV delay falls outside the bounds 206 and 208, adjustments to pacing control parameters and/or pacing mode may be performed to maintain an AV delay within the defined upper and lower bounds 206 and 208. By modulating pacing parameters to maintain the AV delay within the upper and lower bounds 206 and 208, the deleterious effects of atrial contraction against a still-contracting ventricle can be minimized or avoided.

Figure 4:
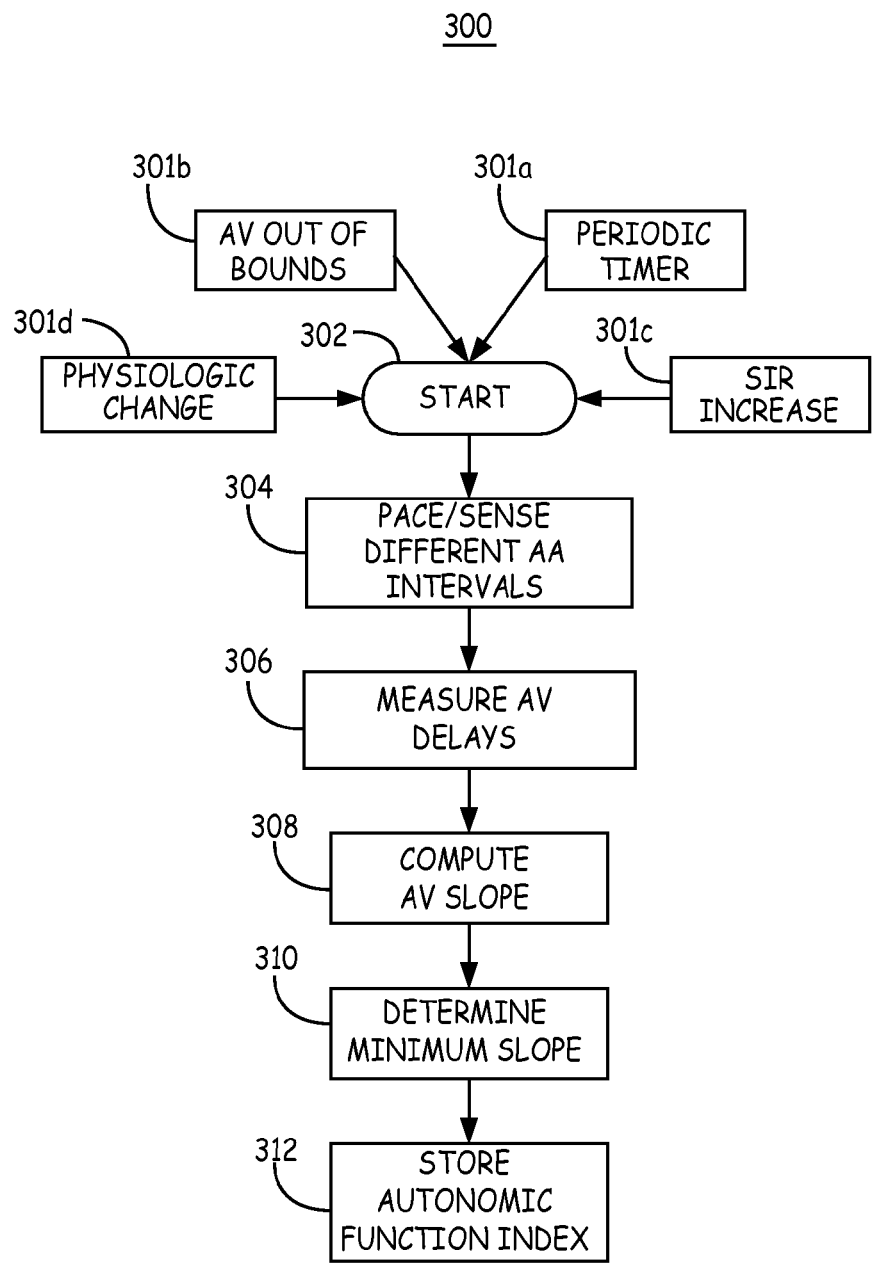
FIG. 4 is a flow chart of one method for monitoring a patient's autonomic function.

FIG. 4 is a flow chart of one method for monitoring a patient's autonomic function. Flow chart 300 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Initiation of method 300 may occur at block 302 on a scheduled basis in response to a periodic timer 301a, for example every 12 hours, daily, weekly or monthly. Alternatively or additionally, method 300 may be initiated at block 302 in response to measuring an AV delay outside predefined upper or lower bounds at block 301b, in response to detecting a need for an increased pacing rate based on a SIR at block 301c, or in response to detection of another physiological change or condition that may reflect a change in autonomic function. Other physiological changes that may be monitored include, for example, heart rate variability and blood pressure.

After initiating method 300 at block 302 in response to one of the conditions at blocks 301a-d, various AA intervals are identified at block 304, and the AV delay is measured at block 306 for at least two different AA intervals. The AA intervals identified at block 300 may be paced AA intervals. The atrium may be paced in a rate responsive mode such that the AA intervals are increasing toward a maximum upper rate or decreasing toward a lower base rate. As the AA intervals are adjusted, the AV delay is measured for different AA intervals.

Alternatively, the atrium may be intentionally paced at different rates according to an autonomic function index measurement algorithm. Pacing pulses may be delivered to the atrium at either increasing or decreasing or random AA intervals to allow the AV delay to be measured for at least two different AA intervals. In one embodiment, atrial pacing is delivered at a first AA interval corresponding to the lower base pacing rate or at a rate slightly above an intrinsic atrial rate and at another, shorter AA interval. The shorter AA interval may be at or near the maximum upper rate or a rate intermediate the lower base rate and the maximum upper rate. Pacing pulses may be delivered at one or more intervening AA intervals to allow a gradual increase (or decrease) between two different AA intervals applied for AV delay measurements to avoid abrupt heart rate changes.

Various AA intervals identified at block 304 may include intrinsic AA intervals measured in the absence of pacing. In one embodiment, intrinsic AA intervals may be monitored and the AV delay may be measured for different AA intervals as they naturally occur. Monitoring of AA intervals over several minutes, hours, an entire day or longer may be required in order to obtain a desired number of AV measurements for a desired number of different AA intervals.

The AV delay may be measured for one or more cardiac cycles for a given AA interval. For example, an AV delay may be measured for 3 or more cardiac cycles at a given AA interval and an average or median AV delay may be determined for the AA interval. The AV delay for a given AA interval may be measured after pacing or sensing the AA interval for more than one cardiac cycle to allow intrinsic adjustment of the AV delay to a new AA interval to occur prior to measuring the AV delay. For example, an AA interval may be applied during atrial pacing for five cardiac cycles, or any other desired number of cardiac cycles, before measuring the AV delay for that AA interval. Alternatively, the AV delay may be measured for each cardiac cycle at a given AA interval following a change in pacing rate to determine how quickly the AV delay adjusts to a new AA interval.

After acquiring AV delay measurements for at least two different AA intervals, the AV delay measurements are used to compute an autonomic function index. In one embodiment, a slope of the AV delays as a function of AA is computed at block 308. If only two AV points are available (for two different AA intervals), a single slope is computed and stored at block 312 as the autonomic function index.

If multiple AV delay data points are available for multiple different AA intervals, multiple slopes may be computed between pairs of neighboring points and/or between non-neighboring points, i.e., points separated by intervening AV/AA points. In one embodiment, a minimum slope measured between adjacent, neighboring AV delay points is determined at block 310. With worsening autonomic function, AV delay plotted as a function of AA interval may show a trend toward a flattened response (AV delay not changing as AA interval changes) or even a negative-going slope (AV delay becoming longer with shortening AA interval, see FIG. 3). As such, determining the minimum slope of the AV delay curve plotted as a function of AA interval will identify a change toward a lower positive slope, near zero or negative-going slope indicating a potential worsening of autonomic function. The minimum slope (i.e. most negative slope or lowest positive slope) may be stored as the autonomic function index at block 312.

Generally, AV delay is expected to change in the same direction (increase or decrease) as any changes in AA interval occur. The magnitude of the change in AV delay relative to a change in AA interval may vary within and between individuals. In some embodiments, determining and storing an automatic function index at blocks 308 and 312 may include, exclusively or additionally, determining the sign of the slope of AV delay as a function AA and storing the sign of the slope as the index. If the slope is negative indicating an opposite change in AV delay with changes in AA interval, the autonomic function may be worsening.

The heart rate at which the slope becomes flat or negative may also be identified. As the patient's autonomic function worsens, the patient may become less tolerant of higher heart rates. As such, storing an autonomic function index may include storing a heart rate and associated slope, or multiple heart rates and slopes, such that the highest heart rate at which a normal AV delay response occurs can be identified or estimated.

It is contemplated that other computations of an autonomic function index using AV delays measured for at least two different AA intervals may be made, which may include computing ratios, differences, slopes or other features of the AV delay measurements as they relate to the AA interval. For example, the difference in AV delay measured for two different AA intervals may be stored and trends in the difference may be determined over time. Furthermore, the rate at which the AV delay adjusts to a change in AA interval may be stored as an autonomic function index. As autonomic function worsens, the number of AA intervals required for the AV delay to adjust appropriately may increase after a change in AA interval.

In some embodiments the method shown in flow chart 300 may be performed to obtain a daytime autonomic function index and a nighttime autonomic function index. Diurnal variation in autonomic function may then be assessed and differences in autonomic function during the day and night may be used for diagnostic and prognostic purposes and may be used in controlling pacing therapies during the day and during the night accordingly.

Figure 5:
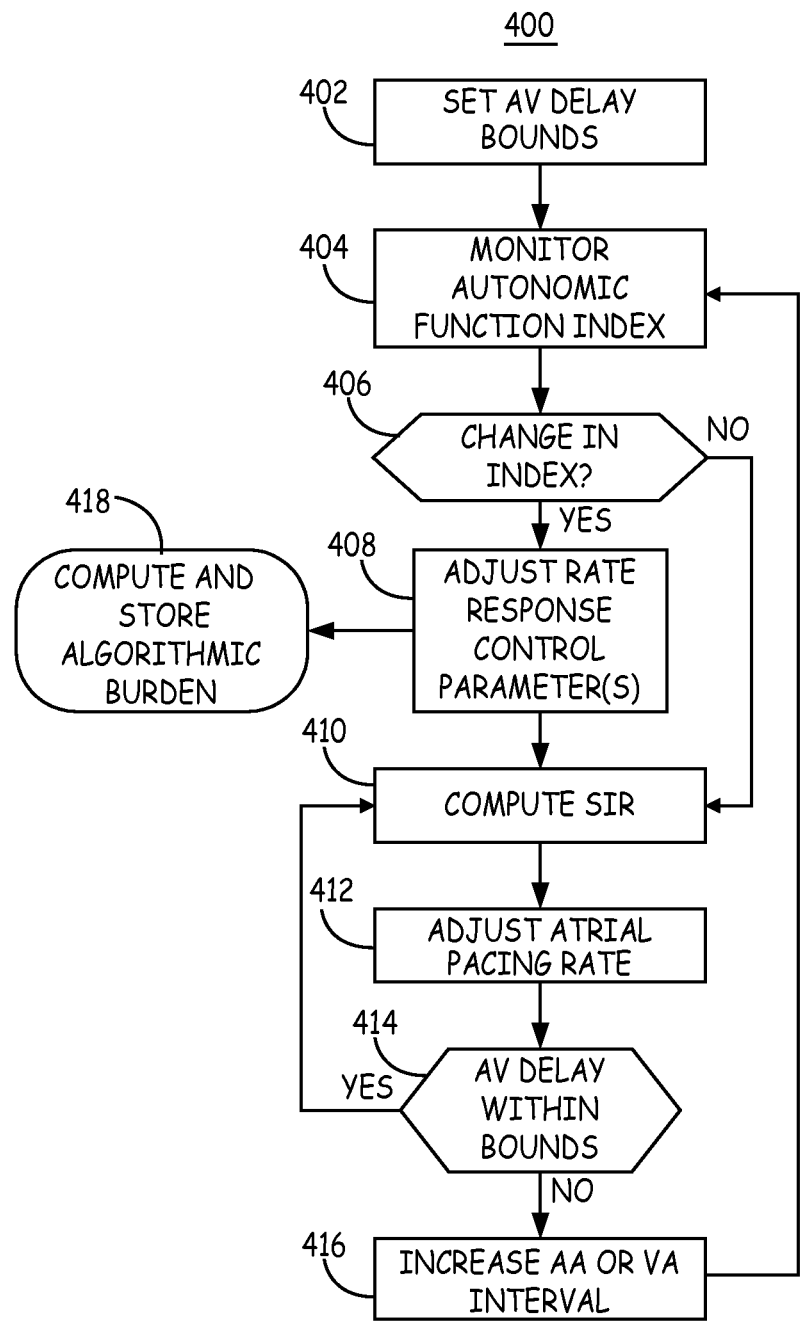
FIG. 5 is a flow chart of a method for controlling cardiac pacing.

FIG. 5 is a flow chart of a method 400 for controlling cardiac pacing. Method 400 includes monitoring an autonomic function index for use in setting rate response control parameters. Additionally or alternatively, AV delay is monitored during atrial pacing to allow dynamic adjustments in pacing parameters to maintain the AV delay within predefined bounds.

AV delay bounds are set at block 402. In one embodiment, AV delay bounds are determined using empirical measurements of intervals corresponding to atrial and ventricular events to define an upper and a lower AV delay bound as a function of atrial pacing rate. A method for defining AV delay bounds will be described below in conjunction with FIG. 6.

At block 404, the autonomic function index is determined as described above in conjunction with FIG. 5. If there is no change in the autonomic function index, as determined at block 406, the implanted device advances to block 410 to provide rate responsive pacing according to currently programmed control parameters. If a change in the autonomic function index is detected, one or more rate response control parameters may be adjusted at block 408 to reduce (or increase) the aggressiveness of the rate response pacing of the device. Examples of programmable parameters used to control the rate response pacing function of an implantable medical device are generally described in U.S. Pat. No. 7,318,968 (Condie, et al.), hereby incorporated herein by reference in its entirety.

A worsening index may be identified at block 406 based on a threshold crossing or a threshold change compared to the previously measured index. A worsening index may correspond to an index that, compared to previously measured index, represents a change from a non-negative to a negative slope of the AV delay as a function of AA, a decrease in a measured slope of AV delay as a function of AA (i.e., less shortening or even lengthening of the AV delay with decreasing AA interval), an index corresponding to a lower heart rate at which a flattened or negative slope of AV delay as a function of AA interval is measured, and/or a greater number AA intervals required for the AV delay to appropriately adjust to a new AA interval.

In response to the worsening index, the maximum upper pacing rate may be decreased at block 408 to prevent disproportionate long AV delays from occurring during short AA intervals. A new maximum upper pacing rate may set at a predetermined decrement from the existing upper rate. Alternatively, the new upper pacing rate may be set at a rate which the AV delay curve changes or inflects toward a flattened or negative slope. In other words, the new upper pacing rate may be set to a pacing rate at which an abnormal AV delay response begins to be observed as the atrial pacing rate is increased.

Additionally or alternatively, a transfer function or look-up table stored in device memory that relates demand sensor output to a sensor indicated rate may be adjusted. The greater the slope of a transfer function defining the relationship between the demand sensor output and the sensor indicated pacing rate, the more aggressive the rate response will be. In some embodiments, the implantable device stores a family of transfer functions or look-up tables which can be selected to provide more or less aggressive rate response. The transfer function or look-up table may be adjusted in response to a worsening autonomic function index at block 408 to provide less aggressive rate responsive pacing.

In some embodiments, dual slope rate response pacing may be provided. Dual slope rate response pacing is controlled in part by programming an activities of daily living (ADL) rate intermediate a programmed lower rate and upper pacing rate. A range of pacing rates occurring between the lower rate and the ADL rate provides a desired rate response during normal daily activities of the patient, such as getting out of bed, moving about the house, etc. If a worsening autonomic function index is measured, one or both of the ADL rate and the upper pacing rate may be decreased at block 408.

The range of pacing rates occurring between the ADL rate and the upper pacing rate defines an exertion range corresponding to more strenuous patient activity. Two different transfer functions or look-up tables may be selected for converting a demand sensor output to a SIR for the two different ADL rate range and exertion rate range. One or both of these transfer functions may be adjusted in response to a change in the autonomic function index at block 408.

Other parameters that may be implemented for controlling rate response pacing include an attack constant which controls how quickly a sensor indicated rate may increase in response to increased demand sensor output. In other words, the attack constant controls how quickly the pacing rate is increased in response to increased demand sensor output. A decay constant may control how quickly the sensor indicated rate may decrease in response to decreased demand sensor output. One or both of the constants may be adjusted to control how quickly the pacing rate changes in response to demand sensor output. By providing more time for the intrinsic system to adjust to a new pacing rate, a more appropriate AV delay response may be reached in a patient having worsened autonomic function then when the pacing rate is allowed to change relatively more quickly.

Figure 6:
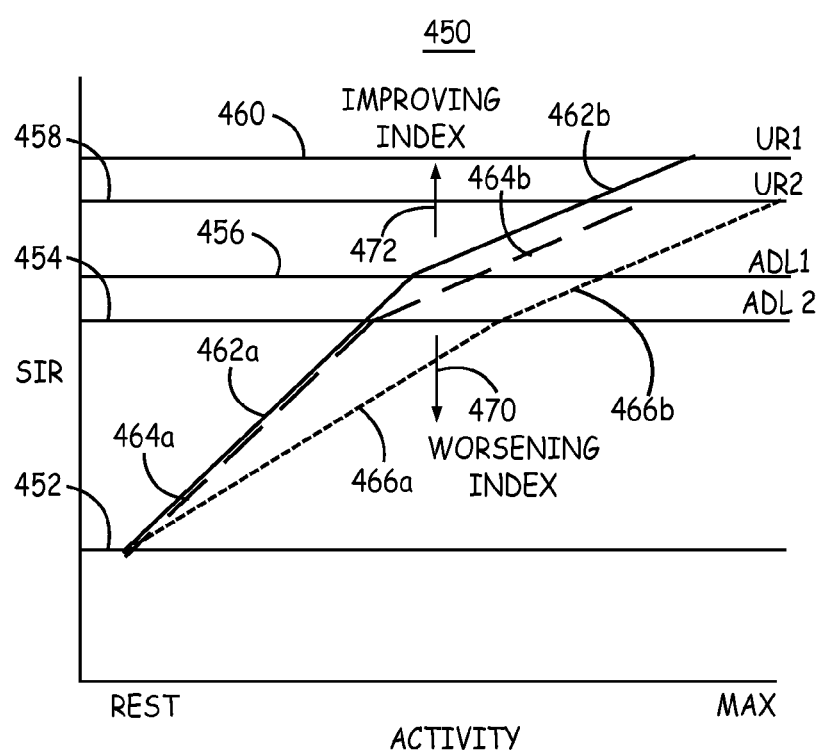
FIG. 6 is a graph of rate response curves illustrating adjustments that may be made in response to changes in the autonomic function index.

FIG. 6 is a graph 450 of rate response curves illustrating adjustments that may be made in response to changes in the autonomic function index. The sensor indicated pacing rate (SIR) is shown as a function of activity used in this example as the demand sensor. Activity sensor output ranges between a resting output and a maximum exertion output. The lower rate 452 is defined as a baseline pacing rate provided at rest. Initially, an activities of daily living (ADL1) rate 456 and an upper rate (UR1) 460 are programmed with selected transfer functions 462*a* and 462*b* relating the demand sensor output to the SIR using a dual slope transfer function defined distinctly over the ADL range and the exertion range. The rate response of the implanted device will follow the transfer functions 462*a* and 462*b* to produce the SIR provided in response to the demand sensor output. The rate of change to a new SIR may be determined by a programmed attack or delay constant.

If a worsening autonomic function index is detected, a number of parameter changes can reduce the aggressiveness of the rate response as generally indicated by arrow 470. By reducing the ADL rate from ADL1 456 to ADL2 454, and/or reducing the UR1 460 to UR2 458, the transfer functions 464*a* and 464*b* shift downward to provide less aggressive rate responsive pacing. The slopes of the transfer functions 464*a* and 464*b* may be kept the same as the respective transfer functions 462*a* and 462*b*, but a less aggressive response is provided by reducing the ADL rate and the UR.

Additionally or alternatively, the slope of the transfer functions may be reduced as represented by the transfer functions 466*a* and 466*b*, which show the effect of reducing the transfer function slope and reducing the ADL rate (from ADL1 456 to ADL2 454) and the maximum upper rate (from UR1 460 to UR2 458). An overall less aggressive rate response pacing therapy is provided.

If the autonomic function index shows improvement, the ADL rate, maximum upper rate, and/or transfer function slopes may be increased to provide a more aggressive rate response as generally indicated by arrow 472.

Returning to FIG. 5, the demand sensor used to compute a SIR may also be changed at block 408 in response to a worsening autonomic function index. The rate responsive pacing device may be provided with more than one demand sensor, each of which may be used individually or in different combinations for computing a SIR. If a change in autonomic function is detected, the pacing device may determine which demand sensor or combination of sensors provides a lower SIR than the demand sensor(s) currently being used to compute SIR. For example, a respiration sensor may provide a lower SIR than an activity sensor or vice versa. In another example, a combination of respiration sensor output and activity sensor output may provide a lower SIR than one or both of the sensors alone. A different demand sensor or combination of demand sensors may be selected which results in a lower SIR than the currently selected sensor(s) used for computing SIR.

At block 410, SIR is updated according to the selected demand sensor output. The atrial pacing rate is adjusted to the SIR according to currently programmed rate response control parameters at block 412, which may have been adjusted at block 408.

During atrial pacing, the AV delay may be monitored at block 414. AV delay monitoring may be performed continuously, periodically, or in response to a pacing rate change. A measured AV delay (which may be a median or average AV delay obtained from multiple cardiac cycles at a common AA interval) may be compared to the predefined AV delay bounds at block 414. As long as the AV delay falls within the predetermined bounds, the implanted device continues to pace the patient according to the presently determined SIR (block 410) and programmed rate response control parameters.

If the AV delay falls outside the AV delay bounds, the pacing parameters may be immediately adjusted at block 416 to modulate the AV delay such that it falls within the AV delay bounds. Adjustments to the pacing parameters may include increasing the AA interval or a VA interval such that the atrial pacing rate is effectively decreased to restore a more normal relationship between the AV delay and AA interval. Though not explicitly shown in FIG. 5, other pacing parameters may be adjusted to restore an appropriate AV delay. Other responses may include a pacing mode switch to DDD pacing to allow ventricular pacing at an appropriate AV interval. However, as mentioned previously, it may be desirable to avoid ventricular pacing, therefore adjustments to the effective atrial pacing rate are generally more physiologically desirable for modulating the AV delay.

The dynamic adjustment of the rate response pacing at block 416 may be performed "on-the-fly" without altering the programmed rate response control parameters described in conjunction with block 408. In other words, the rate response control parameters may remain at the current settings while the pacing escape intervals and/or pacing mode are adjusted to modulate the AV delay to maintain it within the predetermined bounds. If such modulation is required, however, method 400 may return to block 404 to check the autonomic function index or directly to block 408 to make adjustments to the rate response control parameters. Furthermore, it is recognized that monitoring the AV delay and adjusting pacing parameters to maintain the AV delay within predefined bounds may be performed independently of autonomic function index monitoring.

Each time a rate response control parameter, including the demand sensor(s) selected to compute a SIR, is adjusted in response to a worsened autonomic function index at block 408, the adjustment may be logged in memory at block 418. The frequency of changes in rate response control based on the autonomic function index and/or the duration that rate response control parameters are set to adjusted values based on the autonomic function index may be used as indicators of autonomic function. When the rate response parameters are largely controlled based on the autonomic function index (high algorithmic burden), the patient's autonomic function may be poor or worsening.

In some embodiments, the percentage of time that a rate response parameter is set to an adjusted parameter in response to an autonomic function index is tracked at block 418 as an "algorithmic burden". This percentage or burden that an algorithm based on an autonomic function index is operating to control rate response may have diagnostic value to a clinician as an indicator of potentially poor or worsening autonomic function. In other words, the more often or greater percentage of time that rate response control parameters are controlled by an algorithm based on an autonomic function index, the worse the patient's autonomic function may be.

Figure 7:
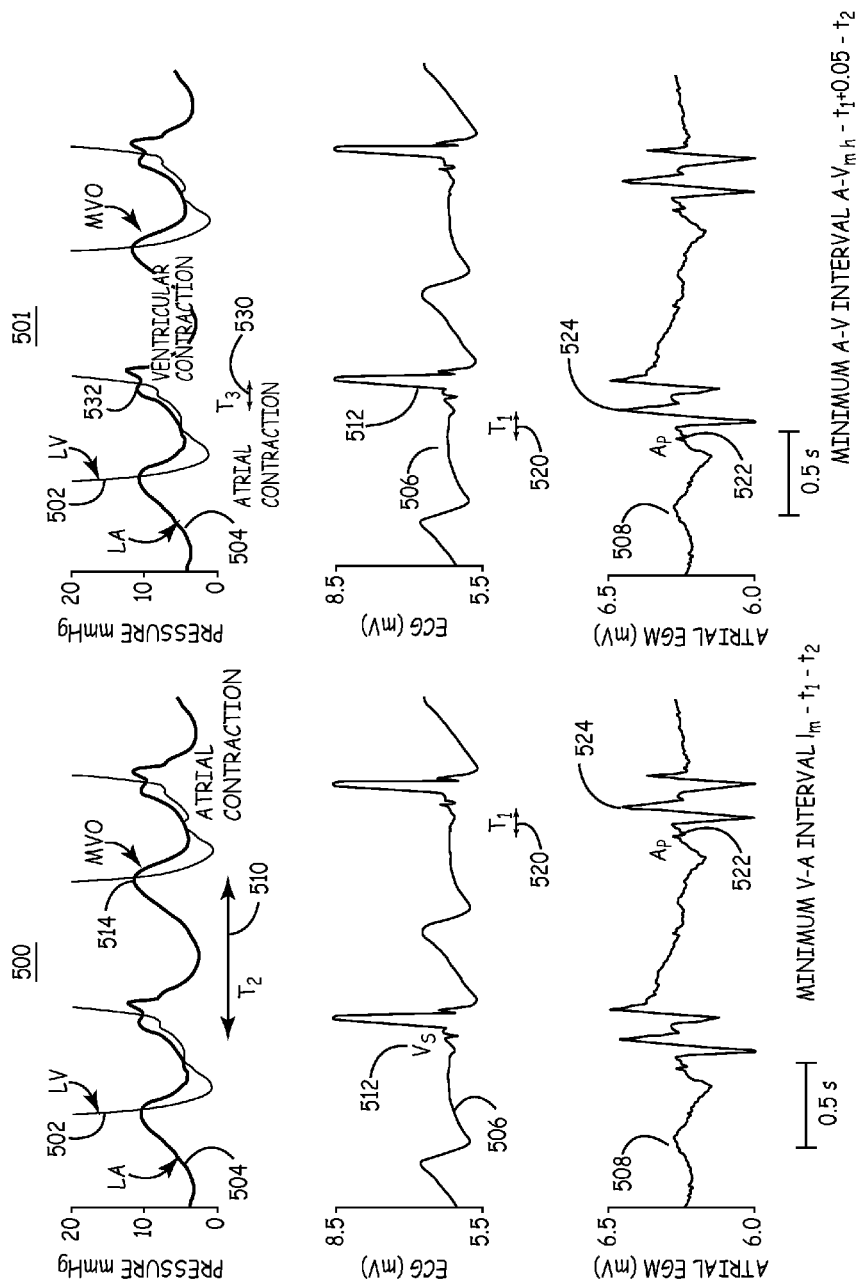
FIGS. 7A and 7B are recordings of EGM signals and intracardiac pressure signals illustrating methods for defining AV delay upper and lower bounds.

FIGS. 7A and 7B are recordings of EGM signals and intracardiac pressure signals illustrating methods for defining AV delay upper and lower bounds. FIG. 7A illustrates a method 500 for computing a maximum AV delay bound. Recordings include the left ventricular (LV) pressure 502, left atrial (LA) pressure 504, ECG 506, and atrial EGM 508. Using these recordings, measurements are made to determine a minimum time interval between a ventricular sense event 512 and the subsequent atrial pacing pulse 522 that avoids atrial mechanical contraction against a closed atrioventricular valve. This minimum VA interval allows a maximum AV delay to be computed for a given AA interval.

Time interval T2 510 is the interval between a ventricular sense event 512 and the time of mitral valve opening 514. The mitral valve opens when the LV pressure 502 falls below the LA pressure 504. Accordingly, one method for measuring T2 includes measuring an intracardiac ventricular pressure signal and an intracardiac atrial pressure. As discussed previously, other physiological signals may be used to detect a time of atrioventricular valve opening.

The time interval T1 is the time from an atrial pacing pulse 522 until atrial mechanical contraction begins and can be referred to as the electromechanical delay. T1 520 may be measured from the atrial pacing pulse 522 until the LA pressure signal 504 begins to increase, as identified for example by an inflection point. The minimum VA interval can be computed as the time T2 510 from the ventricular sense event 512 until mitral valve opening 514 minus the atrial electromechanical delay T1 520. This minimum VA interval is the minimum interval for delivering an atrial pacing pulse after a sensed R-wave to avoid atrial mechanical contraction against a closed mitral valve. Thus the maximum AV interval is:

$$\text{AV maximum} = AA - (T2 - T1)$$

wherein AA is the desired atrial pacing rate and (T2-T1) is the minimum VA interval that promotes atrial contraction against an open mitral valve.

FIG. 7B illustrates a method 501 for computing a minimum AV delay bound. In FIG. 7B, the same reference numbers are used as in FIG. 7A to identify similar elements. The LV pressure 502, LA pressure 504, ECG 506 and atrial EGM 508 are recorded to allow time intervals to be measured for determining a minimum time interval from an atrial pacing pulse 522 until mitral valve closure 532. This minimum time interval corresponds to a minimum desired AV delay that avoids atrial contraction against a closed atrioventricular valve.

The time interval T1 520 is approximately the electromechanical delay between an atrial pacing pulse 522 and the onset of mechanical contraction of the atrium, which may be determined by the start of pressure development in the left atrium. The time required to complete atrial systole, i.e. the time for the atrial tissue to fully contract after depolarization, is assumed to be approximately 50 ms. Thus the total time from the atrial pacing pulse 522 to the end of atrial systole is T1 520 plus the assumed atrial systolic duration of 50 ms.

The ventricular sense event occurs at a time interval T3 530 earlier than mitral valve closure 532. The mitral valve closes at 532 when LV pressure 502 exceeds LA pressure 504. The ventricular mechanical contraction requires time after the ventricular sense event 512 to develop enough pressure to cause mitral valve closure 532. The atrium is preferably done contracting by this time.

Thus, the minimum AV delay that allows the atrium to be finished contracting before mitral valve closure is the total time from the atrial pacing pulse until the end of atrial systole less the time from the R-wave to mitral valve closure. Expressed mathematically, the minimum AV delay can be computed as:

$$\text{AV minimum} = (T1 + 50\ \text{ms}) - T3$$

While specific physiological signals are shown in FIGS. 7A and 7B with regard to determining mitral valve opening and closing relative to ventricular sense events, it is recognized that numerous signals may be used to identify atrioventricular valve opening and closure for determining time intervals corresponding to those illustrated.

Figure 8:
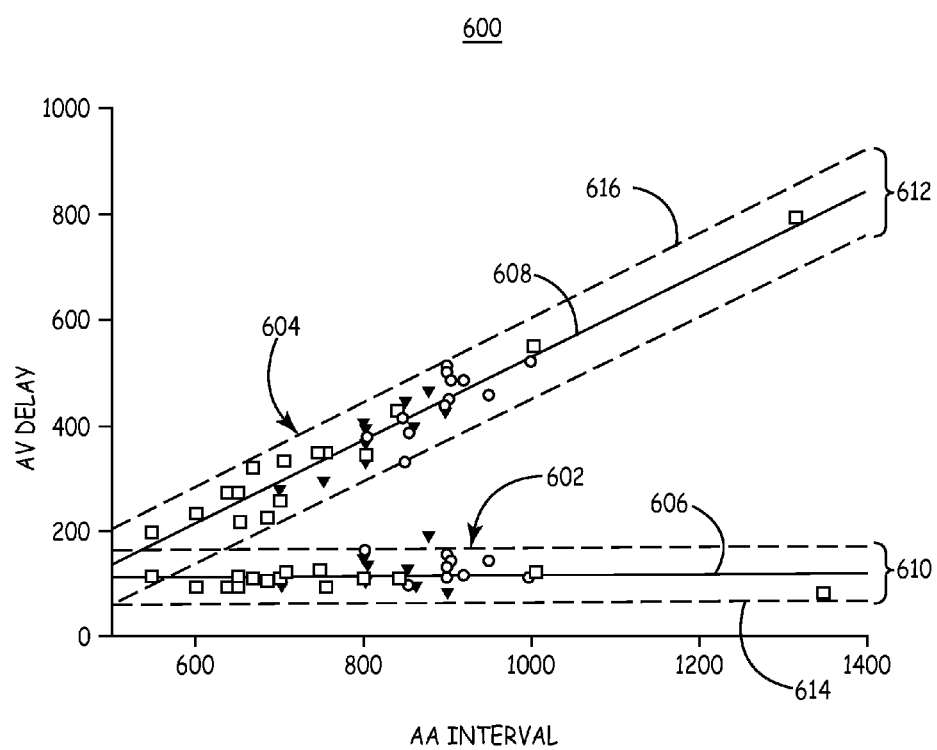
FIG. 8 is a plot of values of minimum and maximum AV delays computed using the time interval measurements illustrated in FIGS. 7A and 7B in patients.

FIG. 8 is a plot 600 of values of minimum and maximum AV delays computed using the time interval measurements illustrated in FIGS. 7A and 7B in patients. The time interval measurements, i.e. T1 520, T2 510, and T3 530 were acquired in 3 different patient populations including patients having diastolic dysfunction with paroxysmal atrial fibrillation, patients having normal left ventricular function, and patients having left ventricular systolic dysfunction. The time interval measurements were used to compute the AV minimum and maximum values according to the equations provided above. Empirically-derived AV delay maximum values 604 and AV delay minimum values 602 are plotted along the y-axis as a function of the heart rate (AA interval) along the x-axis. Linear regression or other curve fitting analysis can be performed to obtain best-fit equations for the empirically-derived AV delay maximum values 604 and AV delay minimum values 602.

In FIG. 8, linear regression analysis AV delay maximum values 604 produced the line 608 and linear regression analysis of AV delay minimum values 602 produced the line 606. Confidence intervals 610 and 612 can be computed from the best-fit analysis to provide outer confidence limits used to define a lower AV delay bound 614 and an upper AV delay bound 616. For the example data shown, an AV delay upper bound is defined by the upper 95% confidence interval limit defined by the line:

AV maximum=0.789(*AA*)−261

An AV delay lower bound is defined by lower the 95% confidence interval limit defined by the line:

AV minimum=0.015(*AA*)+101

In some embodiments, only an AV delay upper bound 616 is determined to allow modulation of atrial-only pacing to maintain the AV delay below the upper bound 616. The probability of AV delay falling below the AV delay lower bound 614 is low when the ventricular depolarization is naturally conducted to the ventricle. However, the lower bound 614 may be used to limit a minimum AV interval used during dual chamber pacing.

In the analysis performed to generate the data shown in FIG. 8, the AV maximum and minimum values computed for the three different patient populations appeared to result in AV maximum and minimum bounds independent of patient population. Thus, empirically-derived AV delay bounds may be applied across different patient populations, tailored to a specific patient population, or tailored to a particular patient when physiological sensor signals are available in an individual patient for making the time interval measurements as indicated in FIGS. 7A and 7B.

Figure 9:
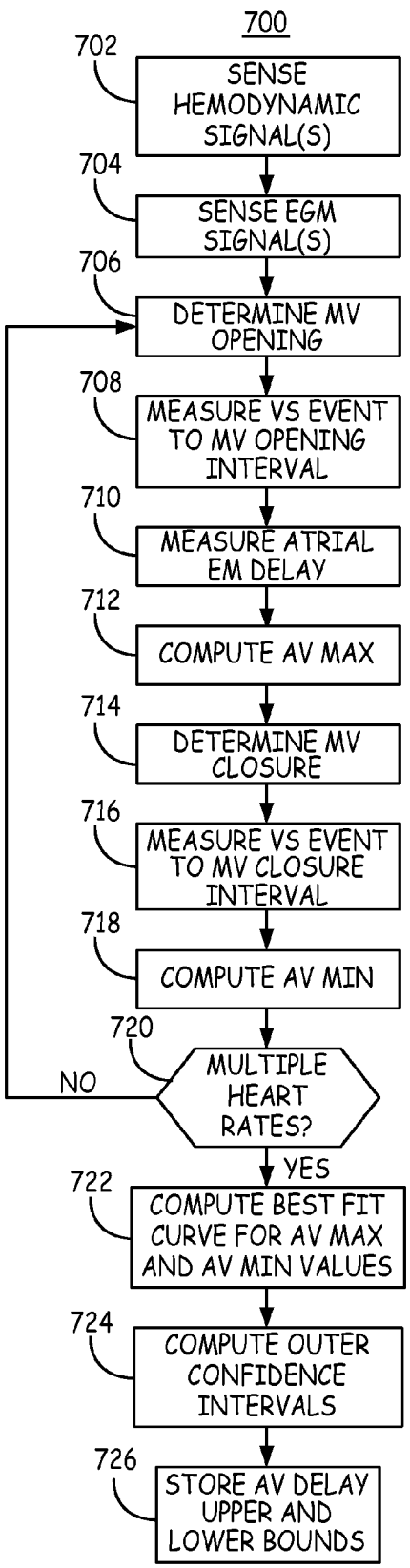
FIG. 9 is a flow chart of a method for defining upper and lower AV delay bounds.

FIG. 9 is a flow chart of one method 700 for defining upper and lower AV delay bounds for use in controlling rate responsive minimum ventricular pacing. At block 702 one or more hemodynamic signals are sensed which enable the timing of atrioventricular valve opening and closure to be estimated. In the example of FIGS. 7A and 7B, the left atrial pressure and the left ventricular pressure are measured and the points at which these pressure signals intersect are identified as mitral valve opening and closing times. Atrioventricular valve opening and closing times may be estimated from other hemodynamic signals such as a right ventricular pressure signal, acoustical signals sensitive to heart sounds, heart wall motion signals, and aortic or pulmonary artery flow signals. Methods described herein are not limited to any particular sensor output for determining or estimating atrioventricular valve opening and closing times.

At block 704 EGM signals (or ECG signals) are sensed. At block 706, the timing of the mitral valve (MV) opening is determined At block 708, the time interval between an R-wave sensed on the EGM signal and the time of the mitral valve opening is measured. The time interval corresponds to T2 510 of FIG. 7A.

At block 710, the atrial electromechanical delay is measured or estimated. The electromechanical delay may be measured from the time of an atrial pacing pulse to an inflection point in the atrial pressure signal indicating an onset of increasing atrial pressure associated with atrial mechanical contraction. In alternative embodiments, an estimated atrial electromechanical delay may be based on clinical data and not specifically measured here.

At block 712, the maximum AV delay is computed based on a minimum VA interval between a ventricular sense event and an atrial pacing pulse resulting in atrial mechanical contraction occurring upon mitral valve opening.

At block 714, the time of mitral valve closure is determined from the hemodynamic signal(s). At block 716, the time interval between a ventricular R-wave sensed on the EGM signal and the mitral valve closure is determined. At block 718, the minimum AV delay is computed as a time interval between an atrial pacing pulse and the mitral valve closing time by summing the atrial electromechanical delay and an estimated atrial systolic duration (physiological time required for the atrium to fully contract), and subtracting the time between a subsequent ventricular sensed event and mitral valve closure. This minimum AV delay promotes completion of atrial contraction upon or prior to mitral valve opening.

Blocks 706 through 718 may be repeated for a desired number of different heart rates to obtain a desired number of minimum and maximum AV delay values. The minimum and maximum AV delay values may be determined for intrinsic heart rates or paced atrial rates controlled to allow minimum and maximum AV delay values to be computed for multiple rates. If minimum and maximum AV delay values have been computed for at least two (or more) different heart rates, as determined at block 720, best fit curves are computed for the maximum AV delay values and for the minimum AV delay values at block 722.

As described previously, the AV delay upper and lower bounds may be computed as outer confidence intervals computed from the best fit curve at block 724. For example, the upper 90%, 95% or other confidence interval determined for the maximum AV delay best fit curve may define the AV delay upper bound. The lower 90%, 95% or other confidence interval determined for the minimum AV delay best fit curve may define the AV delay lower bound. The AV delay upper and lower bounds may alternatively be defined based on a percentage of or fixed margin from the best fit curves.

At block 726, the upper and lower AV delay bounds are stored in device memory and used to compare measured AV delays during atrial pacing. When a measured AV delay falls outside the AV delay bounds, adjustment of the atrial pacing is performed to modulate the AV delay within the upper and lower bounds.

Figure 10:
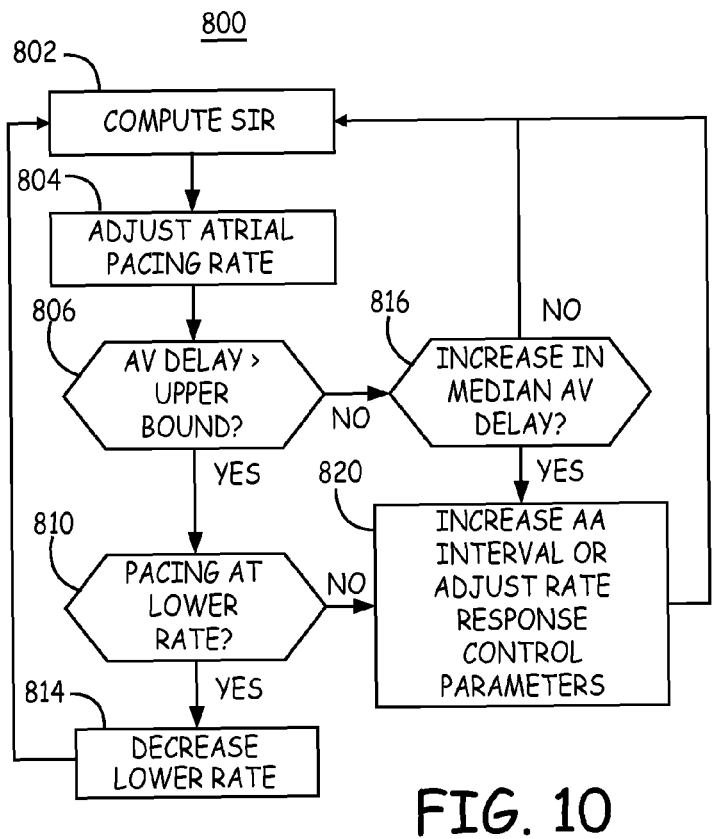
FIG. 10 is a flow chart summarizing one method for modulating AV delay during atrial-only pacing.

FIG. 10 is a flow chart summarizing one method 800 for modulating AV delay during atrial-only pacing. Assuming rate responsive pacing is enabled, the sensor indicated pacing rate is computed at block 802. The atrial pacing rate is adjusted at block 804 according to the SIR and the currently programmed rate response control parameters.

The AV delay is monitored at block 806 during the atrial pacing by measuring the time interval between atrial pacing pulses and subsequent R-waves sensed on an EGM signal. The AV delay is compared to an atrial-rate dependent upper bound at block 806. The upper bound may be stored as a linear (or non-linear) function of AA interval, as generally described in conjunction with FIGS. 8 and 9. The atrial-rate dependent upper bound may alternatively be stored in the form of a look-up table, with each entry calculated from empirically-derived upper boundary equations.

If the measured AV delay is greater than the stored upper bound for the current atrial pacing rate, as determined at block 806, and if the device is currently pacing at the programmed lower rate (block 810), the lower rate is decreased at block 814. This situation of long AV delay during lower rate pacing may occur during the night with worsening autonomic function and circadian variation in autonomic function. Accordingly, a lower pacing rate may be greater than what is needed for the patient and may be resulting in poor atrio-ventricular coupling due to long AV delay. As such, the lower rate is decreased to restore a more appropriate AV delay for a given AA interval. The AV delay may be rechecked and additional adjustments to the lower rate may be made as necessary.

Figure 11:
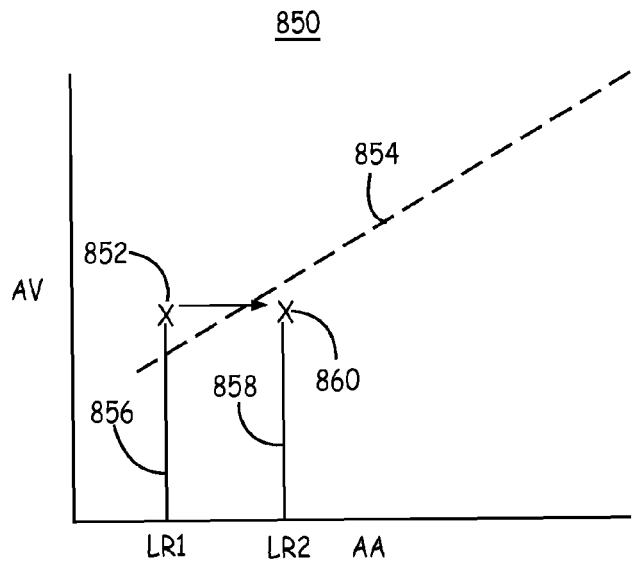
FIG. 11 is a graph of AV delay illustrating adjustment of the AA interval to shift a monitored AV delay within an upper AV delay bound.

The lower rate may be decreased in predetermined decrements down to a programmed minimum until the AV delay is within the upper bound. Alternatively, the adjusted lower rate may be determined based on the current AV delay and the stored AV delay upper bound. For example, using the measured AV delay, an AA interval which shifts the AV delay within the upper bound limit may be computed from a stored upper bound function or identified from a stored look-up table. An example of this adjustment is illustrated in FIG. 11.

An AV delay 852 measured during atrial pacing at a programmed lower rate (LR1) 856 exceeds an AV delay upper bound 854. Using the stored upper bound curve 854 (or look-up table generated using the curve 854), an AA interval 860 is identified which shifts the measured AV delay to the right, within the upper bound 854. The lower pacing rate is decreased from LR1 856 to LR2 858 corresponding to the identified longer AA interval 860. The AV delay may be rechecked and additional adjustments to the lower rate may be made as necessary. Thus monitoring of the AV delay relative to an AV delay upper bound allows both daytime rate responsive pacing and nighttime bradycardia pacing to be adjusted to modulate the AV delay within acceptable bounds during atrial only pacing.

Returning to FIG. 10, if the AV delay exceeds the upper bound (block 806) and the device is not pacing at the lower rate (block 810), the AA interval may be increased or other rate response control parameters may be adjusted (block 820) to restore an AV delay within the upper bound. The AA interval may be increased by a predetermined increment or adjusted to an interval computed using the upper bound curve and measured AV delay to shift the measured AV delay within the upper bound.

The median AV delay may additionally or alternatively be monitored to detect sudden increases in the AV delay. In one embodiment, if the AV delay does not exceed the upper bound, a median of the AV delay is compared at block 816 to a previously determined median AV delay to determine if the AV delay has suddenly increased. The median AV delay for a given AA interval may be computed over a predetermined number of AA intervals, e.g. 3 intervals, 8 intervals, 12 intervals etc. The difference between the current median and the immediately preceding median is computed. The difference is compared to a threshold and if the threshold is exceeded a sudden increase in AV delay is detected. In one embodiment, a "sudden" increase in AV delay refers to an AV delay that increases by approximately 50 to 80 ms within 2 to 5 AA intervals. In other embodiments, a sudden increase may be an AV delay that increases by more than approximately 50 ms following a first atrial pacing event subsequent to an atrial sensed event. A sudden increase in AV delay may represent a poor autonomic response to an increased heart rate.

If the AV delay median is determined to suddenly increase, the AA interval is increased and/or other rate response control parameters are adjusted. The AV delay may be rechecked and additional adjustments made as needed. It is contemplated that monitoring the median AV delay for sudden increases may be performed with or without monitoring of the AV delay relative to an upper bound.

Thus, a device and methods for monitoring autonomic function and modulating the AV delay during atrial pacing have been presented in the foregoing description with reference to specific embodiments. It is appreciated that various modifications to the referenced embodiments may be made without departing from the scope of the disclosure as set forth in the following claims.

The invention claimed is:

1. An implantable medical device, comprising:
   an atrial pacing and sensing lead for delivering atrial pacing pulses and sensing atrial events;
   a ventricular event sensor for sensing ventricular events;
   a therapy delivery module coupled to the atrial pacing and sensing lead for delivering cardiac pacing pulses;
   a diagnostics module coupled to the atrial pacing and sensing lead and the ventricular event sensor, the diagnostics module measuring a first AV delay using a sensed ventricular event corresponding to a first AA interval, the diagnostics module computing an autonomic function index using the first AV delay;
   a medical report module compiling the autonomic function index in a diagnostic report;
   a metabolic demand sensor; and
   a control module coupled to the diagnostics module, the therapy delivery module and the metabolic demand sensor and configured to determine a sensor indicated pacing rate in response to the demand sensor, control the therapy delivery module to deliver rate responsive pacing in response to the sensor indicated pacing rate, and adjust a parameter used to determine the sensor indicated pacing rate in response to detecting a change in the autonomic function index.

2. The implantable medical device of claim 1 wherein the diagnostics module measures a second AV delay corresponding to a second AA interval and computes the autonomic function index using the first and second AV delays.

3. The implantable medical device of claim 2 wherein the diagnostics module computes the autonomic function index as a slope between the first AV delay and the second AV delay plotted as a function of AA interval.

4. The implantable medical device of claim 1 wherein the diagnostic module computes a first autonomic function index using an AV delay measurement during a daytime interval of time and a second autonomic function index using an AV delay measurement during a nighttime interval of time.

5. The implantable medical device of claim 2, wherein the diagnostic module is configured to control the therapy delivery module to deliver atrial pacing pulses at a plurality of AA intervals and the first and second AV delays are measured in response to the plurality of paced AA intervals.

6. The implantable medical device of claim 1, further comprising:
   the control module configured to reduce the aggressiveness of the rate responsive pacing in response to detecting a worsening autonomic function index by adjusting the parameter used to compute the sensor indicated rate to cause the sensor indicated rate to lowered.

7. The implantable medical device of claim 1, wherein adjusting the parameter comprises adjusting a maximum atrial pacing rate.

8. The implantable medical device of claim 1, wherein adjusting the parameter comprises adjusting an activities of daily living rate.

9. The implantable medical device of claim 1, wherein adjusting the parameter comprises adjusting a rate response transfer function relating a demand sensor output to an atrial pacing rate.

10. The implantable medical device of claim 1, further comprising a plurality of demand sensors,
    the control module configured to select from the plurality of demand sensors at least one demand sensor signal for computing the sensor-indicated rate,
    the control module configured to adjust the parameter by adjusting selection of the demand sensor signal in response to the change in the autonomic function index.

11. The implantable medical device of claim 1, wherein the diagnostics module determines an algorithmic burden as one of a time duration or a frequency of the parameter being adjusted in response to a change in the autonomic function index.

12. The implantable medical device of claim 3 wherein determining the autonomic function index further comprises determining a heart rate at which a change in a slope of AV delay as a function of AA interval occurs.

13. The implantable medical device of claim 1, further comprising a memory storing an AV delay bound,
wherein the diagnostics module monitors AV delay relative to the AV delay bound during atrial pacing and adjusts the atrial pacing in response to a monitored AV delay falling outside of the AV delay bound.

14. The implantable medical device of claim 13 wherein the control module adjusts control parameters used to control atrial pacing in response to the monitored AV delay falling outside the AV delay bound.

15. The implantable medical device of claim 13 wherein the AV delay bound is an upper AV delay bound and the control module decreases a lower pacing rate in response to the monitored AV delay exceeding the upper AV delay bound during pacing at the lower pacing rate.

16. The implantable medical device of claim 14 wherein the diagnostics module computes an AA interval using the stored bound and the monitored AV delay, the computed AA interval corresponding to the monitored AV delay falling within the AV delay bound, the control module adjusting the atrial pacing rate based on the computed AA interval.

17. The implantable medical device of claim 13 further comprising a physiological sensor providing output corresponding to atrioventricular valve opening and closure;
the diagnostics module using the physiological sensor output for determining a time interval corresponding to a closed atrioventricular valve and computing an AV delay bound based on the time interval.

18. The implantable medical device of claim 5 wherein the diagnostics module determines a median AV delay for a predetermined number of consecutive AA intervals, compares the median AV delay to a previous median AV delay, and adjusts a pacing control parameter in response to a threshold difference between the median AV delay and the previous median AV delay.

19. A computer readable medium storing a set of instructions which when implemented in an implantable medical device system cause the system to:
deliver atrial pacing pulses;
sense ventricular events;
measure an AV delay using a sensed ventricular event corresponding to an AA interval;
compute an autonomic function index using the AV delay;
compile the autonomic function index in a diagnostic report; and
enable a control module coupled to a diagnostics module, a therapy delivery module and a metabolic demand sensor to determine a sensor indicated pacing rate in response to the demand sensor, control the therapy delivery module to deliver rate responsive pacing in response to the sensor indicated pacing rate, and adjust a parameter used to determine the sensor indicated pacing rate in response to the diagnostics module detecting a change in the autonomic function index.

20. A method for use in an implantable medical device, the method comprising:
delivering atrial pacing pulses;
sensing ventricular events;
measuring an AV delay using a sensed ventricular event corresponding to an AA interval;
computing an autonomic function index using the AV delay;
compiling the autonomic function index in a diagnostic report; and
enabling a control module coupled to a diagnostics module, a therapy delivery module and a metabolic demand sensor to determine a sensor indicated pacing rate in response to the demand sensor, control the therapy delivery module to deliver rate responsive pacing in response to the sensor indicated pacing rate, and adjust a parameter used to determine the sensor indicated pacing rate in response to the diagnostics module detecting a change in the autonomic function index.

21. A medical device, comprising;
a pacing and sensing lead for delivering pacing pulses and sensing cardiac events;
a therapy delivery module coupled to the pacing and sensing lead for delivering cardiac pacing pulses;
a diagnostics module configured to compute an autonomic function index;
a metabolic demand sensor; and
a control module coupled to the diagnostics module, the therapy delivery module and the metabolic demand sensor and enabled to determine a sensor indicated pacing rate in response to the demand sensor, control the pacing module to deliver rate responsive pacing in response to the sensor indicated pacing rate, and adjust a parameter used to determine the sensor indicated pacing rate in response to the diagnostics module detecting a change in the autonomic function index.

22. The device of claim 1, wherein the control module is further configured to adjust a rate of change in response to detecting a change in the autonomic function index, the rate of change controlling the rate the therapy delivery module changes from the sensor indicated rate to a next sensor indicated rate in response to a change in an output of the demand sensor.

* * * * *